United States Patent [19]
Benazzi et al.

[11] Patent Number: 5,986,156
[45] Date of Patent: Nov. 16, 1999

[54] ZEOLITE BASED CATALYST OF MODIFIED MAZZITE STRUCTURE TYPE AND ITS USE FOR THE DISMUTATION AND/OR TRANSALKYLATION OF ALKYLAROMATIC HYDROCARBONS

[75] Inventors: Eric Benazzi, Montesson; Fabio Alario, Neuilly sur Seine, both of France

[73] Assignee: Institut Francais du Petrole, France

[21] Appl. No.: 09/055,264

[22] Filed: Apr. 6, 1998

Related U.S. Application Data

[63] Continuation-in-part of application No. 08/797,786, Feb. 7, 1997, abandoned.

[30]   Foreign Application Priority Data

Feb. 9, 1996 [FR]   France .................................. 96 01604

[51] Int. Cl.$^6$ ...................................................... C07C 5/22
[52] U.S. Cl. .............................. 585/475; 502/64; 502/66; 502/85; 502/86
[58] Field of Search .............................. 585/475; 502/64, 502/66, 85, 86

[56]   References Cited

U.S. PATENT DOCUMENTS 5,210,356   5/1993   Shamshoum et al. .

FOREIGN PATENT DOCUMENTS 0 082 211   6/1983   European Pat. Off. .
0 537 347   12/1983  European Pat. Off. .
0 214 042   3/1987   European Pat. Off. .

*Primary Examiner*—Thomas Dunn
*Attorney, Agent, or Firm*—Millen, White, Zelano, & Branigan, P.C.

[57]   ABSTRACT

The invention concerns a catalyst comprising at least one matrix and at least one zeolite of structure type mazzite, preferably omega zeolite, comprising silicon and aluminium, at least partially, preferably practically completely in its acid form, said zeolite having been prepared by dealuminization of the framework, by means of at least one treatment using at least one solution of a fluorosilicate of a cation in a proportion of 0.05 to 5 moles per mole of aluminium contained in the dry zeolite, said catalyst optionally comprising at least one element selected from groups IB and VIII of the periodic classification of the elements. The invention also concerns the use of said catalyst for the dismutation of alkylaromatic hydrocarbons, and preferably for the dismutation of toluene to produce benzene and xylenes, and/or for the transalkylation of alkylaromatic hydrocarbons, preferably for the transalkylation of toluene and trimethylbenzenes to produce xylenes.

19 Claims, No Drawings

5,986,156

ZEOLITE BASED CATALYST OF MODIFIED MAZZITE STRUCTURE TYPE AND ITS USE FOR THE DISMUTATION AND/OR TRANSALKYLATION OF ALKYLAROMATIC HYDROCARBONS

CROSS REFERENCE TO RELATED APPLICATION

This invention is a continuation in part of application Ser. No. 08/797,786 filed Feb. 7, 1997, now abandoned, based on French application Ser. No. 96/01.604 filed Feb. 9, 1996.

The invention concerns a catalyst comprising- at least one matrix and at least one zeolite of structure type mazzite, preferably omega zeolite, comprising silicon and aluminum, at least partially, preferably practically completely in its acid form, said zeolite having, been prepared by dealuminization of the framework, by means of at least one treatment using at least one solution of a fluorosilicate of a cation in a proportion of 0.05 to 5 moles per mole of aluminum contained in the dry zeolite, said catalyst optionally comprising, at least one element selected from groups IB and VIII of the periodic classification of the elements. The invention also concerns the use of said catalyst for the dismutation of alkylaromatic hydrocarbons, and preferably for the dismutation of toluene to produce benzene and xylenes, and/or for the transalkylation of alkylaromatic hydrocarbons, preferably for the transalkylation of toluene and trimethylbenzenes to produce xylenes.

SUMMARY OF THE INVENTION

Numerous dismutation and transalkylation catalysts based on mordenite have been described in the prior art. The mordenite used has a monodimensional microporous network with a pore diameter of 7×6.5 Å (1 Å=1 Angstrom=1×10$^{-10}$ m) ("Atlas of Zeolite Structure Types", W. M. Meier and D. H. Olson, 3$^{rd}$ edition, 1992). This is the case in U.S. Pat. No. 3,506,731 where a mordenite in its hydrogen form is used and in French patent application FR-A-2 367 533. This is also the case in U.S. Pat. No. 3,281,483) which mentions mordenites which are exchanged essentially with silver or nickel ions, or in U.S. Pat. No. 3,780,121 which describes a mordenite exchanged with metals from group IB of the periodic classification of the elements and which is characterized by a Si/Al atomic ratio which is in the range 6 to 40; U.S. Pat. No. 3,629,351 also concerns a mordenite containing ions of metals from groups IB, VA, VIA, IIA and VIII of the periodic classification of the elements.

BACKGROUND OF THE INVENTION

The mazzite present in the catalyst of the invention can optionally have undergone post-synthesis modifications such as dealuminization by means of at least one treatment with at least one solution comprising at least one fluorosilicate salt such as ammonium hexafluorosilicate, as described in U.S. Pat. No. 4,503,023, which describes such a treatment for a number of zeolites and, depending on the nature of the zeolite, can produce a degree of dealuminization of at least 30%, or European patent application EP-A-0 573 347, which concerns a mordenite based catalyst thus modified, the concentration of the salt being particularly low with respect to that used in the previous patent, and its use for the isomerization of alkylaromatic compounds containing 8 carbon atoms per molecule.

Surprisingly, a catalyst comprising at least one matrix and at least one zeolite of structure type mazzite, at least partially acid, which has been prepared by at least one treatment with at least one solution of a fluorosilicate of a cation in a proportion of 0.05 to 5 moles per mole of aluminum contained in the dry zeolite, preferably between 0.06 and 4 moles per mole of aluminum contained in the dry zeolite, said prepared zeolite having an Si/Al ratio of the external surface of the zeolite crystals increased of a percentage comprised between 10 and 500%, preferably between 30 and 400% as compared to the Si/Al ratio of the starting zeolite. The catalyst optionally comprising at least one element selected from groups IB and VIII of the periodic classification of the elements, results in improved catalytic performances with respect to prior art catalysts, in particular as regards selectivities, for the dismutation reactions of alkylaromatic hydrocarbons such as toluene, and/or for the transalkylation of alkylaromatic hydrocarbons such as toluene and trimethylbenzenes.

The invention concerns a catalyst comprising at least one matrix (or binder) and at least one zeolite of structure type mazzite, preferably omega zeolite, at least partially, preferably practically completely, in its acid form, comprising silicon and aluminum, which zeolite has been prepared by at least one treatment using at least one solution of a fluorosilicate of a cation in a proportion of 0.05 to 5, preferably 0.06 to 4 moles per mole of aluminium contained in the dry zeolite, said prepared zeolite having an Si/Al ratio of the external surface of the zeolite crystals increased of a percentage comprised between 10 and 500%, preferably between 30 and 400% as compared to the Si/Al ratio of the starting zeolite. The catalyst optionally comprising at least one element selected from the group formed by groups IB and VIII of the periodic classification of the elements.

The matrix is generally selected from members of the group formed by clays (for example from natural clays such as kaolin or bentonite), magnesia, aluminas, silicas, titanium oxide, boron oxide, zirconia, aluminum phosphates, titanium phosphates, zirconium phosphates and silica-aluminas, preferably from members of the group formed by aluminas and clays.

The zeolite with structure type mazzite of the invention is generally selected from the group formed by omega zeolite, mazzite, LZ-202 zeolite or ZSM-4 zeolite, preferably omega zeolite, with a principal pore diameter of about 7.4 Å and with a monodimensional microporous network ("Atlas of Zeolite Structure Types", W. M. Meier and D. H. Olson, 3$^{rd}$ edition. 1992).

The framework dealuminization step by treatment with at least one solution comprising at least one fluorosilicate salt can optionally take place after a more conventional extraction step such as the dealuminization step described in U.S. Pat. No. 4,780,436.

The catalyst of the invention generally contains 10% to 99%. preferably 20% to 95%, of zeolite with structure type mazzite, preferably omega zeolite, at least partially, preferably practically completely in its acid form. When the catalyst of the present invention contains at least one element selected from the group formed by groups IB and VIII of the periodic classification of the elements, the content of said element(s) is generally in the range 0.01% to 10% by weight, preferably in the range 0.05% to 7% by weight, and more preferably in the range 0.10% to 5% by weight. The complement to 100% generally consists of the matrix in the catalyst.

The invention also concerns the preparation of said zeolite with structure type mazzite and said catalyst.

The zeolite with structure type mazzite comprised in the catalyst used in accordance with the invention, comprising silicon and aluminum, has a global Si/Al atomic ratio in the range 3.2 to 100, preferably in the range 6 to 80, and more preferably in the range 8 to 60, also a sodium content of less than 0.6% by weight with respect to the dry zeolite weight, preferably less than 0.1% by weight.

The zeolite with structure type mazzite of the invention is prepared by dealuminization of an unrefined synthesized zeolite with structure type mazzite using any method which is known to the skilled person, in particular the method described in U.S. Pat. No. 4,780,436 when T is aluminum, i.e., a calcining step is carried out in a stream of dry air, to eliminate the organic structuring agent occluded in the microporosity of the zeolite, followed by at least one ion exchange step using at least one $NH_4NO_3$ solution, to eliminate practically all alkaline cations, in particular sodium, present in the cationic position in the zeolite, then at least one framework dealuminization cycle comprising at least one calcining step in the presence of steam at a temperature which is generally in the range 550° C. to 850° C., followed by at least one acid attack step.

The zeolite undergoes at least one treatment with at least one dilute cation fluorosilicate solution, preferably at least one dilute solution of ammonium hexafluorosilicate, generally comprising between 0.05 and 5, preferably between 0.06 and 4, moles per aluminum mole present in the dry zeolite. The external Si/Al ratio is specifically increased, in a percentage of at least 10% and at most 500% and preferably at least 30% and at most 400% as compared to the Si/Al ratio of the starting zeolite.

The framework dealuminization cycle for the zeolite with structure type mazzite, comprising at least one calcining step carried out in steam and at least one attack step in an acid medium, can be repeated as many times as is necessary to obtain the dealuminized zeolite with structure type mazzite with the desired characteristics. Similarly, following calcining in steam, a number of successive acid attack steps using different concentrations of acid solutions can be carried out.

The fluorosilicate used as the dealuminizing agent for the zeolitic framework and as a source of silicon, thus allowing re-insertion of silicon atoms into the crystalline network of the zeolite in place of the aluminum atoms which are extracted, is selected from fluorosilicate salts with the following formula: $M_{2/x}SiF_6$ where M is a metallic or non-metallic cation with valency x. The cation M can thus be selected from the group formed by $NH_4^+$, ammonium alkyls, $K^+$, $Na^+$, $Li^+$, $Ba^{2+}$, $Mg^{2+}$, $Cd^{2+}$, $Cu^+$, $Cu^{2+}$, $Ca^{2+}$, $Cs^{30}$, $Fe^{2+}$, $Co^{2+}$, $Pb^{2+}$, $Mn^{2+}$, $Rb^+$, $Ag^+$, $Sr^{2+}$, $Zn^{2+}$, $Ti^+$ and $H^+$.

Preferably, ammonium hexafluorosilicate is used as it leads to the formation of the ammonium salt $(NH_4)_3AlF_6$ which is soluble in water and can thus be eliminated easily. In general, the temperature at which the zeolite with structure type mazzite is treated with ammonium hexafluorosilicate is in the range 20° C. to 100° C., preferably in the range 50° C. to 100° C. The quantities of ammonium hexafluorosilicate used are calculated with respect to a zeolite which is dried in a stream of air, at 450° C., for 4 hours. The zeolite with structure type mazzite is treated in the presence of ammonium acetate which buffers the pH of the reaction medium to values which are in the range 4 to 8, preferably in the range 5.5 to 7. at which pH values the Framework of the zeolite is not destroyed by direct acid attack.

After addition of the ammonium hexafluorosilicate solution to the suspension of the zeolite of structure type mazzite in an ammonium acetate solution, the reaction mixture is vigorously stirred at the desired temperature for a period which is in the range 30 minutes to 48 hours, preferably in the range 1 to 2 hours.

The zeolite with structure type mazzite is then filtered at the reaction temperature and washed with abundant quantities of boiling water. The volume of boiling water used to carry out the washes corresponds to v/w=150 ml/g (the ratio v/w is the ratio of the volume of boiling water to the quantity of dry zeolite treated).

After this treatment, the zeolite with modified structure type mazzite undergoes heat treatment to decompose the ammonium cations present in the network and obtain the acid form of the zeolite.

Thus the zeolite with structure type mazzite obtained has a sodium content of less than 2000 ppm by weight with respect to the weight of dry omega zeolite, and a global Si/Al atomic ratio which is in the range 3.2 to 100, preferably in the range 6 to 80, and more preferably in the range 8 to 60.

The external Si/Al ratio of the zeolite thus obtained is in the range of 10 to 500% and preferably 30 to 400% more than the unmodified zeolite.

The characteristics of the zeolite with structure type mazzite can be measured by the following techniques:
the Si/Al atomic ratio is determined by X ray fluorescence and by silicon 29 nuclear magnetic resonance,
the sodium content is determined by atomic absorption;
the elementary cell volume and crystallinity are determined by X ray diffraction, the omega zeolite sample being prepared as described in the method in standard ASTM D3942 80 set up for faujasite.

The catalyst can be prepared using any method which is known to the skilled person. In general, it is obtained by mixing the matrix and the zeolite then forming. The optional element from the group formed by groups IB and VIII of the periodic classification of the elements can be introduced either before forming, or during mixing, or to the zeolite itself before mixing it, or, as is preferable, after forming. Forming is generally followed by calcining, generally at a temperature which is in the range 250° C. to 600° C. The optional element from the group formed by groups IB and VIII of the periodic classification of the elements can be introduced after said calcining step. In all cases, the element is generally chosen to be deposited either, as is preferable, practically completely on the zeolite, or practically completely on the matrix, or partially on the zeolite and partially on the matrix, the choice being effected, in a manner which is known to the skilled person, by means of the parameters used during said deposition, such as the nature of the precursor selected to effect said deposition.

The element from groups IB or VIII, preferably selected from the group formed by Ag, Ni and Pt, and more preferably Ni, can also be deposited on the zeolite-matrix mixture which has been pre-formed using any procedure which is known to the skilled person. Such deposition is generally carried out by the techniques of dry impregnation, ion exchange(s) or co-precipitation. When ion exchange is carried out using precursors based on silver, nickel or platinum, the salts which are generally used are silver salts such as chlorides or nitrates, a tetramine complex of platinum, or nickel salts such as chlorides, nitrates, acetates or formates. The ion exchange technique can also be used to deposit the metal directly on the zeolite powder before optional mixing with a matrix.

When the catalyst contains a plurality of metals, these latter can be introduced either in the same way or using different techniques, before or after forming and in any order. When the technique used is ion exchange, a plurality of successive exchanges may he necessary to introduce the required quantities of metals.

As an example, one preferred method for preparing the catalyst of the invention consists of mixing the zeolite in a wet matrix gel (generally obtained by mixing at least one acid and a matrix powder), for example alumina, for the time required to obtain good homogeneity of the paste thus produced, i.e., for about ten minutes, for example, then passing the paste through a die to form extrudates with a diameter which is, for example, in the range 0.4 to 4 mm. After oven drying for several minutes at 100° C. and after calcining, for example for 2 hours at 400° C. the optional element, for example nickel, can be deposited, for example by ion exchange, said deposit being followed by final calcining, for example for 2 hours at 400° C.

The catalyst of the invention is generally formed so that the catalyst is preferably in the form of pellets, aggregates, extrudates or spherules, depending on its use.

Catalyst preparation is generally finished by calcining, termed final calcining, normally at a temperature which is in the range 250° C. to 600° C. preferably preceded by drying, for example oven drying, at a temperature which is generally in the range from ambient temperature to 250° C. preferably in the range 40° C. to 200° C. The drying step is preferably carried out during the period of temperature rise required to carry out the calcining step.

The invention also concerns the use of the catalyst for the dismutation of alkylaromatic hydrocarbons, preferably for the dismutation of toluene to produce benzene and xylenes, and/or for the transalkylation of alkylaromatic hydrocarbons. preferably transalkylation of generally $C_9^+$ alkylaromatic hydrocarbons (i.e., containing at least 9 carbon atoms per molecule), such as transalkylation and/or dismutation of toluene and/or C), alkylaromatics to produce xylenes. The feed for such a process can comprise 0 to 100% of $C_9^+$ alkylaromatics and 0 to 100% of toluene.

The operating conditions are generally as follows: a temperature which is in the range 250° C. to 600° C., preferably in the range 330° C. to 500° C.: a pressure which is in the range 10 to 60 bar, preferably in the range 20 to 45 bar; a supply space velocity, expressed in kilograms of feed introduced per kilogram of catalyst per hour, in the range 0.1 to 10, preferably in the range 0.5 to 4: and a hydrogen to hydrocarbons molar ratio which is in the range 2 to 20, preferably in the range 3 to 12.

The following examples illustrate the invention without in any way limiting its scope.

EXAMPLE 1

Preparation of Ω1 Zeolite in Accordance with the Invention

The starting material used was an omega zeolite with a global Si/Al atomic ratio of 3.2, a sodium content of about 5.3% with respect to the weight of dry omega zeolite, an elementary cell volume of 2.196 nm$^3$ and a pore volume in nitrogen of 0.125 cm$^3$ liquid per gram, measured at –196° C. and at $P/P_0=0.19$.

This omega zeolite was initially "dry" calcined at 550° C. in a stream of air and nitrogen for 6 hours. The solid obtained was then subjected to three ion exchange steps in a 10 N $NH_4NO_3$ solution at about 100° C. for 4 hours for each exchange step. The omega zeolite then underwent hydrothermal treatment in the presence of 50% of steam at 625° C. for 4 hours. The zeolite underwent acid attack with 1.5 N nitric acid at about 100° C. for 4 hours, to extract the extra-network aluminum species formed during hydrothermal treatment. The volume V of the nitric acid used (in ml) was 10 times the weight W of the dry omega zeolite (V/W=10).

At the end of these treatments, the omega zeolite in its H form had a global Si/Al atomic ratio of 11.3. a framework Si/Al ratio of 12 determined by $^{29}Si$ NMR, an Si/Al ratio of the external surface of the omega zeolite crystals of 15, a sodium content of 160 ppm by weight with respect to the weight of dry omega zeolite, an elementary cell volume of 2.145 nm$^3$ and a nitrogen adsorption capacity of 0.214 cm$^3$ of liquid/g, measured at –196° C. and at $P/P_0=0.19$.

The omega zeolite obtained above was then treated with an ammonium hexafluorosilicate solution. 20 grams of dry zeolite was suspended in 200 ml of an ammonium acetate solution (25 grams of ammonium acetate for 200 ml of distilled water). This suspension was placed in a 500 ml three-necked flask provided with a reflux condenser and a mechanical stirrer. The initial pH of the medium was 6.9. The temperature was raised to 80° C. Using a pump, 95 ml of a 0.5 M ammonium hexafluorosilicate solution was introduced at a rate of 20 ml/h per gram of dry treated zeolite, i.e., a solution flow rate of 6.67 ml/min. Finally, the quantity of ammonium hexafluorosilicate injected represented 1.71 moles of ammonium hexafluorosilicate per mole of aluminum present in the dry omega zeolite. The system was kept at the reaction temperature for another 2 hours. The solution was then cooled to ambient temperature, and the pH measured at the end of the reaction was 5.8. The solid was filtered and washed with at least 4 liters of boiling distilled water, i.e., at least 200 ml of distilled water per gram of dry zeolite (V/W=200 ml/g). The treated zeolite was oven dried at 105° C. overnight then calcined in dry air to remove ammonia from the omega zeolite and obtain the H form. The solid obtained at the end of these treatments was referred to as Ω1. This omega zeolite, Ω1, had a global Si/Al ratio of 15.8. determined by X ray fluorescence, and an Si/Al ratio of the external surface of the zeolite crystals of 43. determined by XPS. The Si/Al ratio of the external surface of the zeolite crystals has been increased of 65%.

EXAMPLE 2

Preparation of Catalyst C1, in Accordance with the Invention

The Ω1 zeolite from Example 1 was formed by extrusion with an alumina gel to obtain catalyst C1 after drying and calcining in dry air. Catalyst C1 contained 80% by weight of omega zeolite and 20% by weight of alumina.

EXAMPLE 3

Preparation of Catalyst C2 of the Invention

In this example, catalyst C1 prepared in Example 2 underwent three ion exchange steps with a nickel acetate solution to introduce 1.0% by weight of nickel into the catalyst.

To this end, catalyst C1 was brought into contact with a 0.5 M solution of $Ni(CH_3CO_2)_2$ at ambient temperature, with stirring. Between each exchange, the solid was separated from the impregnating solution and washed with abundant quantities of deionized water. The concentration of impregnating solution was re-adjusted to 0.5 moles per liter for each exchange.

The wet solid was dried at 120° C. for 12 hours and calcined in a stream of dry air at 500° C. for one hour. Catalyst C2 obtained contained 79.30% by weight of omega zeolite in its hydrogen form, 19.80% by weight of alumina and 0.85% by weight of nickel.

EXAMPLE 4

Preparation of Catalyst C3, not in Accordance with the Invention

The starting material used was an omega zeolite with a global Si/Al atomic ratio of 3.2, a sodium content of about 5.3% with respect to the weight of dry omega zeolite, an elementary cell volume of 2.196 nm³ and a pore volume in nitrogen of 0.125 cm³ liquid per gram, measured at −196° C. and at $P/P_0=0.19$.

This omega zeolite was initially "dry" calcined at 550° C. in a stream of air and nitrogen for 6 hours. The solid obtained was then subjected to three ion exchange steps in a 10 N $NH_4NO_3$ solution at about 100° C. for 4 hours for each exchange step. The omega zeolite then underwent hydrothermal treatment in the presence of 50% of steam at 625° C. for 4 hours. The zeolite underwent acid attack with 1.5 N nitric acid at about 100° C. for 4 hours, to extract the extra-network aluminum species formed during hydrothermal treatment. The volume V of the nitric acid used (in ml) was 10 times the weight W of the dry omega zeolite (V/W=10).

At the end of these treatments, the omega zeolite in its H form had a global Si/Al atomic ratio of 11.3, a framework Si/Al ratio of 12, determined by $^{29}$Si NMR, a sodium content of 160 ppm by weight with respect to the weight of dry omega zeolite, an elementary cell volume of 2.145 nm³ and a nitrogen adsorption capacity of 0.214 cm³ of liquid/g, measured at −196° C. and at $P/P_0=0.019$.

The zeolite obtained above was then formed by extrusion with an alumina gel to obtain catalyst C3, after drying and calcining in dry air, which catalyst contained 80% by weight of omega zeolite and 20% of alumina.

EXAMPLE 5
Preparation of Catalyst C4, not in Accordance with the Invention

In this example, catalyst C3 prepared in Example 4 underwent three ion exchange steps with a nickel acetate solution to introduce 1% by weight of nickel into the catalyst.

To this end, catalyst C3 was brought into contact with a 0.5 M solution of $Ni(CH_3CO_2)_2$ at ambient temperature, with stirring. Between each exchange, the solid was separated from the impregnating solution and washed with abundant quantities of deionized water. The concentration of impregnating solution was re-adjusted to 0.5 moles per liter for each exchange.

The wet solid was dried at 120° C. for 12 hours and calcined in a stream of dry air at 500° C. for one hour. Catalyst C4 obtained contained 79.30% by weight of omega zeolite in its hydrogen form, 19.80% by weight of alumina and 0.85% by weight of nickel.

EXAMPLE 6
Evaluation of Catalyst Performances

The catalysts were used in a fixed bed reactor under pressure, into which the feed, constituted by pure toluene, was introduced.

The table below compares the yields of (benzene+ethylbenzene+xylenes) obtained using catalysts C1 and C2, in accordance with the invention, and C3 and C4, not in accordance with the invention:

Comparison of catalysts C1 and C3 with catalysts C2 and C4 show that the catalysts of the invention, C1 and C2, lead to (benzene+ethylbenzene+xylenes) 1 5 yields which are greater than those obtained with non-conforming catalysts C3 and C4.

The preceding examples can be repeated with similar success, using the generically and specifically described reactants and operating conditions discussed above.

The entire disclosure of all applications, patents and publications, cited above and below, and of corresponding French Application 96/01.604 filed Feb. 9, 1996, is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

We claim:

1. A catalyst comprising at least one matrix and at least one zeolite having a mazzite structure at least partially in its acid form, comprising silicon and aluminum, which has been prepared by subjecting a starting zeolite to at least one dealuminizing step of calcining in the presence of steam followed by at least one step of contacting with an acid in solution and to at least one treatment using at least one solution of a fluorosilicate of a cation in a proportion of 0.05 to 5 moles per mole of aluminum contained in the dry zeolite, the resulting zeolite having an external Si/Al ratio increased by 10 to 500% as compared to the starting zeolite.

2. A catalyst according to claim 1 optionally comprising at least one element selected from the group consisting of the elements of groups IB and VIII of the periodic classification of the elements.

3. A catalyst according to claim 2, in which said element is selected from the group consisting of Ag, Pt and Ni.

4. A catalyst according to claim 2, wherein the element is deposited on the catalyst after forming the matrix and zeolite together.

5. A catalyst according to claim 1, in which said zeolite is selected from the group consisting of gallosilicate mazzite zeolite, mazzite, LZ-202 zeolite, omega zeolite, and ZSM-4 zeolite.

6. A catalyst according to claim 1, in which said zeolite is omega zeolite.

7. A catalyst according to claim 1, wherein the fluorosilicate of a cation is of the following formula: $M_{2/x}SiF_6$, where M is a metallic or non-metallic cation with valency x.

8. A catalyst according to claim 7, in which cation M is selected from the group consisting of $NH_4^+$, ammonium alkyls, $K^+$, $Na^+$, $Li^+$, $Ba^{2+}$, $Mg^{2+}$, $Cd^{2+}$, $Cu^+$, $Cu^{2+}$, $Ca^{2+}$, $Cs^+$, $Fe^{2+}$, $Co^{2+}$, $Pb^{2+}$, $Mn^{2+}$, $Rb^+$, $Ag^+$, $Sr^{2+}$, $Zn^{2+}$, $Tl^+$ and $H^+$.

9. A catalyst according to claim 1, in which the fluorosilicate of a cation is ammonium hexafluorosilicate.

10. A catalyst according to claim 1, comprising 10% to 99% of zeolite and, when said catalyst contains at least one

| Catalysts | C1 (invention) | C3 (not invention) | C2 (invention) | C4 (not invention) |
|---|---|---|---|---|
| Reaction temperature (° C.) | 450 | 450 | 430 | 430 |
| Total reaction pressure (bar) | 30 | 30 | 40 | 40 |
| Yields, % by weight (benzene + ethylbenzene + xylenes) | 38.6 | 38.0 | 37.1 | 36.3 | element selected from the group consisting of the elements of groups IB and VIII of the periodic classification of the elements, between 0.01% and 10% of said element, the complement to 100% by weight consisting of the catalyst matrix.

11. A catalyst according to claim 1, in the form of pellets, aggregates, extrudates or spherules.

12. A catalyst according to claim 1, wherein the treatment using at least one solution of a fluorosilicate of a cation is conducted at a pH in the range of from 4 to 8.

13. A catalyst according to claim 1, wherein the catalyst has additionally been calcined at a temperature of from 250 to 600° C. after the at least one dealuminizing step and at least one treatment using at least one solution of a fluorosilicate cation.

14. A catalyst according to claim 1, wherein the resulting zeolite has an external Si/Al ratio increased by 30 to 400% compared to the starting zeolite.

15. A catalyst according to claim 1, wherein the calcining in the presence of steam is conducted at a temperature of from 550 to 850° C.

16. A catalyst according to claim 1, wherein the treatment using at least one solution of a fluorosilicate of a cation is conducted at a temperature of from 20 to 100° C.

17. A catalyst according to claim 1, wherein the zeolite has a global Si/Al atomic ratio in the range of 3.2 to 100.

18. A method for the dismutation and/or transalkylation of an alkylaromatic compound which comprises dismutating and/or transalkylating the compound in the presence of a catalyst according to claim 1.

19. A method according to claim 18, wherein the alkylaromatic compound is toluene or an alkylaromatic containing at least 9 carbon atoms per molecule.

* * * * *